(12) United States Patent
Duke et al.

(10) Patent No.: US 12,243,651 B2
(45) Date of Patent: Mar. 4, 2025

(54) SYSTEMS AND METHODS FOR AUTOMATICALLY DISPLAYING PATTERNS IN BIOLOGICAL MONITORING DATA

(71) Applicant: Roche Diabetes Care, Inc., Indianapolis, IN (US)

(72) Inventors: David L. Duke, Fishers, IN (US); Paul J. Galley, Cumberland, IN (US); Abhishek S Soni, Indianapolis, IN (US); Mark Mears, Westfield, IN (US); Steven Bousamra, Carmel, IN (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 1666 days.

(21) Appl. No.: 13/912,318

(22) Filed: Jun. 7, 2013

(65) Prior Publication Data
US 2014/0365136 A1 Dec. 11, 2014

(51) Int. Cl.
*G16H 50/70* (2018.01)
*G16H 40/63* (2018.01)
*G16Z 99/00* (2019.01)

(52) U.S. Cl.
CPC ............. *G16H 50/70* (2018.01); *G16H 40/63* (2018.01); *G16Z 99/00* (2019.02)

(58) Field of Classification Search
None
See application file for complete search history.

(56) References Cited

U.S. PATENT DOCUMENTS

2004/0162678 A1   8/2004   Hetzel et al.

FOREIGN PATENT DOCUMENTS

| WO | 2004043230 A2 | 5/2004 |
| WO | 2010075350 A1 | 7/2010 |

*Primary Examiner* — Joseph Woitach
(74) *Attorney, Agent, or Firm* — Dinsmore & Shohl LLP

(57) ABSTRACT

Systems and methods for automatically displaying patterns in biological data may include one or more processors, and machine readable instructions. The machine readable instructions can cause the one or more processors to divide biological data into segments of interest. The one or more processors can transform, automatically, each of the segments of interest into a set of features according to a mathematical algorithm. Further, the one or more processors can cluster, automatically, the segments of interest into groups of clustered segments according to a clustering algorithm. The segments of interest can be grouped in the groups of clustered segments based at least in part upon the set of features. A cluster center can be associated with one of the groups of clustered segments. Moreover, the one or more processors can present, automatically, the cluster center on a human machine interface.

21 Claims, 9 Drawing Sheets

SYSTEMS AND METHODS FOR AUTOMATICALLY DISPLAYING PATTERNS IN BIOLOGICAL MONITORING DATA

CROSS-REFERENCE TO RELATED APPLICATIONS

The present U.S. utility application is related to and claims the priority benefit to patent cooperation treaty patent application serial no. PCT/EP2011/006091, filed Dec. 6, 2011, which claims priority to U.S. provisional patent application No. 61/420,800, filed Dec. 8, 2010. The contents of each of these applications are hereby incorporated by reference in their entirety into this disclosure.

TECHNICAL FIELD

The present specification generally relates to systems and methods for automatically displaying patterns in biological monitoring data and, in some embodiments, to systems and methods for automatically displaying patterns in glucose monitoring data.

BACKGROUND

Biological monitoring data can provide health care providers (HCPs) and patients with ambulatory data that can be utilized to treat and/or manage a medical condition related to biological data. For example, continuous glucose monitoring (CGM) can provide glucose data related to the amount of glucose contained within the blood of a person with diabetes (PwDs). The glucose data can be indexed to time and/or any other method suitable to correlate the glucose data to contextual data such as, for example, meal tags, time of day, day-of-the-week, and the like.

The identification of patterns within the glucose data can be useful for altering patient behavior or patient therapy. For example, HCPs and/or PwDs can identify patterns in the glucose data by sorting based upon the contextual data. However, contextual data is often unavailable. Moreover, HCPs and/or PwDs may not have enough information available to effectively and efficiently make use of all of the available contextual data, i.e., available data patterns can be overlooked.

SUMMARY

The present disclosure comprises systems and methods for automatically displaying patterns in glucose data.

In at least one embodiment of the present disclosure, a collection system for automatically displaying patterns in glucose data may include one or more processors, an electronic display and machine readable instructions. The electronic display can be communicatively coupled to the one or more processors. The machine readable instructions can be executed by the one or more processors. Further, the machine readable instructions can cause the one or more processors to: receive a glucose data signal indicative of ambulatory glucose levels sampled over time; divide the glucose data signal into segments of interest; transform, automatically, each of the segments of interest into a set of features according to a mathematical algorithm, and/or cluster, automatically, the segments of interest into groups of clustered segments according to a clustering algorithm. The segments of interest can be grouped in the groups of clustered segments based at least in part upon the set of features. A cluster center can be associated with one of the groups of clustered segments. The cluster center can be based upon a mean the one of the groups of clustered segments. The machine readable instructions can also cause the one or more processors to present, automatically, the cluster center on the electronic display.

In at least one embodiment of the present disclosure, a method for automatically displaying patterns in biological monitoring data is described that may include receiving biological data indicative of ambulatory biological information sampled over time from one or more subjects. The biological data may include a time index. Further, the biological data may be divided into segments of interest according to the time index. Each of the segments of interest can be transformed, automatically with one or more processors, into a set of features according to a mathematical algorithm. The segments of interest can be clustered, automatically with one or more processors, into groups of clustered segments according to a clustering algorithm. The clustering algorithm can calculate a distance metric based at least in part upon the set of features of each of the segments of interest such that similar segments of interest are grouped in one of the groups of clustered segments. The clustering algorithm can calculate a cluster center that is associated with one of the groups of clustered segments. The cluster center can be based upon a mean of the one of the groups of clustered segments. Moreover, the cluster center can be presented, automatically with the one or more processors, with a human machine interface.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

As used herein with the various illustrated embodiments described below, the following terms include, but are not limited to, the following meanings.

The term "signal" means a waveform (e.g., electrical, optical, magnetic, mechanical or electromagnetic), such as DC, AC, sinusoidal-wave, triangular-wave, square-wave, vibration, and the like, capable of traveling through a medium.

The phrase "communicatively coupled" means that components are capable of exchanging data signals with one another such as, for example, electrical signals via conductive medium, electromagnetic signals via air, optical signals via optical waveguides, and the like.

The term "sensor," as used herein, means a device that measures a physical quantity and converts it into a data signal, which is correlated to the measured value of the physical quantity, such as, for example, an electrical signal, an electromagnetic signal, an optical signal, a mechanical signal, and the like.

The term "continuous" means substantially uninterrupted for a period of time. Accordingly, continuous data can be data that is sampled in a substantially uninterrupted manner for a period of time, i.e., the data can be sampled at a set and/or varying sample rate with minimal interruption.

The term "glucose meter" means any device to determine continuously or discontinuously a glucose level in a body fluid such as blood or interstitial fluid. Such devices are well known for a person having ordinary skills in the art.

The term "medication delivery device" means e.g. an insulin pump, or patch pump, an insulin pen or a glucose delivery device, in particular realized as a pump or combinations of insulin and glucose delivery systems. It is also possible in some examples for the device to deliver another medication to a person wherein the medication influences the person's glucose level.

Figure 1:
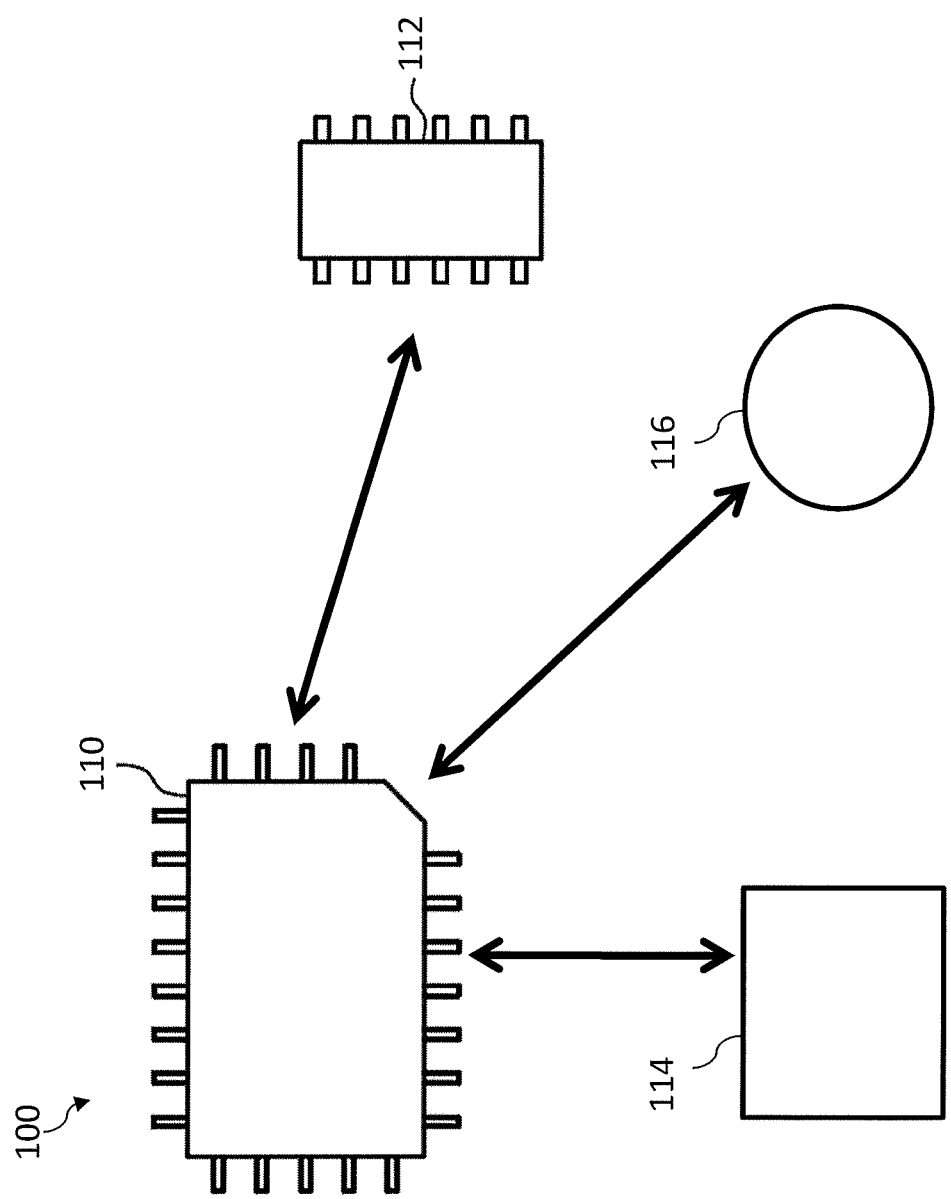
FIG. 1 schematically depicts a system for automatically displaying patterns in biological data according to one or more embodiments shown and described herein.

FIG. 1 generally depicts at least one embodiment of a system for automatically displaying patterns in biological data (e.g., glucose data). The system generally comprises one or more processors, a human machine interface communicably coupled to the one or more processors, and machine readable instructions that are executed by the one or more processors to automatically display patterns in biological data. Various embodiments of the system for automatically displaying patterns in biological data and methods for automatically displaying patterns in biological data will be described in more detail herein.

Referring now to FIG. 1, the system 100 for automatically displaying patterns in biological data comprises one or more processors 110 for executing machine readable instructions and automatically directing components communicatively coupled (generally indicated in FIG. 1 as double arrowed lines) to the one or more processors 110. The one or more processors 110 can optionally be communicatively coupled to a memory 112 for storing machine readable instructions. The one or more processors 110 may be a controller, an integrated circuit, a microchip, a computer, or any other computing device capable of executing machine readable instructions. The memory 112 may be RAM, ROM, a flash memory, a hard drive, or any device capable of storing machine readable instructions.

In the embodiments described herein, the one or more processors 110 may be integral with a single component of the system 100. However, it is noted that the one or more processors 110 may be separately located within discrete components such as, for example, a glucose meter, a medication delivery device, a mobile phone, a portable digital assistant (PDA), a mobile computing device such as a laptop, a tablet, or a smart phone, a desktop computer, or a server e.g. via a cloud or web based technologies and communicatively coupled with one another without departing from the scope of the present disclosure. It is to be appreciated that in at least one embodiment of the mobile computing device which is useful with one or more embodiments disclosed herein, such a device may include a touch screen and the computing ability to run computational algorithms and/or processes, such as those disclosed herein, and applications, such as an electronic mail program, a calendar program for providing a calendar, as well as provide cellular, wireless, and/or wired connectivity and one or more of the functions of a blood glucose meter, a digital media player, a digital camera, a video camera, a GPS navigation unit, and a web browser that can access and properly display web pages. Accordingly, the system 100 may include a plurality of components each having one or more processors 110 that are communicatively coupled with one or more of the other components. Thus, the systems 100 may utilize a distributed computing arrangement to perform any or the machine readable instructions described herein.

The system 100 further comprises a human machine interface 114 communicatively coupled to the one or more processors 110 for receiving signals from the one or more processors 110 and presenting graphical, textual and/or auditory information. The human machine interface may include an electronic display such as, for example, a liquid crystal display, thin film transistor display, light emitting diode display, a touch screen, or any other device capable of transforming signals from a processor into an optical output, or a mechanical output, such as, for example, a speaker, a printer for displaying information on media, and the like.

Embodiments of the present disclosure also comprise machine readable instructions that includes logic or an algorithm written in any programming language of any generation (e.g., 1GL, 2GL, 3GL, 4GL, or 5GL) such as, e.g., machine language that may be directly executed by the processor, or assembly language, object-oriented programming (OOP), scripting languages, microcode, etc., that may be compiled or assembled into machine readable instructions and stored on a machine readable medium. Alternatively, the logic or algorithm may be written in a hardware description language (HDL), such as implemented via either a field-programmable gate array (FPGA) configuration or an application-specific integrated circuit (ASIC), and their equivalents. Accordingly, the machine readable instructions may be implemented in any conventional computer programming language, as pre-programmed hardware elements, or as a combination of hardware and software components. Moreover, machine readable instructions can be distributed over various components that are communicatively coupled such as, for example, via wires, via a wide area network, via a local area network, via a personal area network, and the like. Thus, any components of the system 100 can transmit signal over the Internet or World Wide Web).

Referring still to FIG. 1, the system 100 may optionally include a biological sensor 116 communicatively coupled to the one or more processors 110 for providing biological data indicative of properties of an analyte. In one embodiment, the biological sensor 116 can be a glucose sensor configured to detect glucose levels (e.g., glucose concentrations) when placed just under the skin of a PwD. For example, the biological sensor 116 can in some embodiments be a disposable glucose sensor that is worn under the skin for a few days until replacement is needed. As is noted above, the biological sensor 116 can be communicatively coupled with the one or more processors 110, which can be located within various discrete components. Accordingly, in the case of a glucose sensor, the biological sensor 116 can be communicatively coupled with, for example, a smart glucose meter, or a medication delivery device and can provide ambulatory CGM data, i.e., glucose data that is sampled continuously throughout the lifetime of the sensor. It is noted that, while the embodiments described herein make reference to blood glucose, the biological sensor 116 can be any sensor that detects biological data related to the treatment and/or management a medical condition related biological data. Furthermore, it is noted that the embodiments described herein can utilize data provided by any discrete component communicatively coupled to the one or more processors 110. Moreover, the biological data can be stored and provided to the one or more processors 110 after a delay of any duration, i.e., the embodiments described herein can be performed offline. Accordingly, the biological data can be aggregated from a population of multiple test subjects.

According to the embodiments described herein, the one or more processors 110 can execute machine readable instructions to automatically display patterns in biological data. As is described in greater detail herein, the biological data can be combined with continuous data, semi-continuous data, and discrete data from any component communicatively coupled to the one or more processors 110 to automatically display patterns within the biological data.

Figure 2:
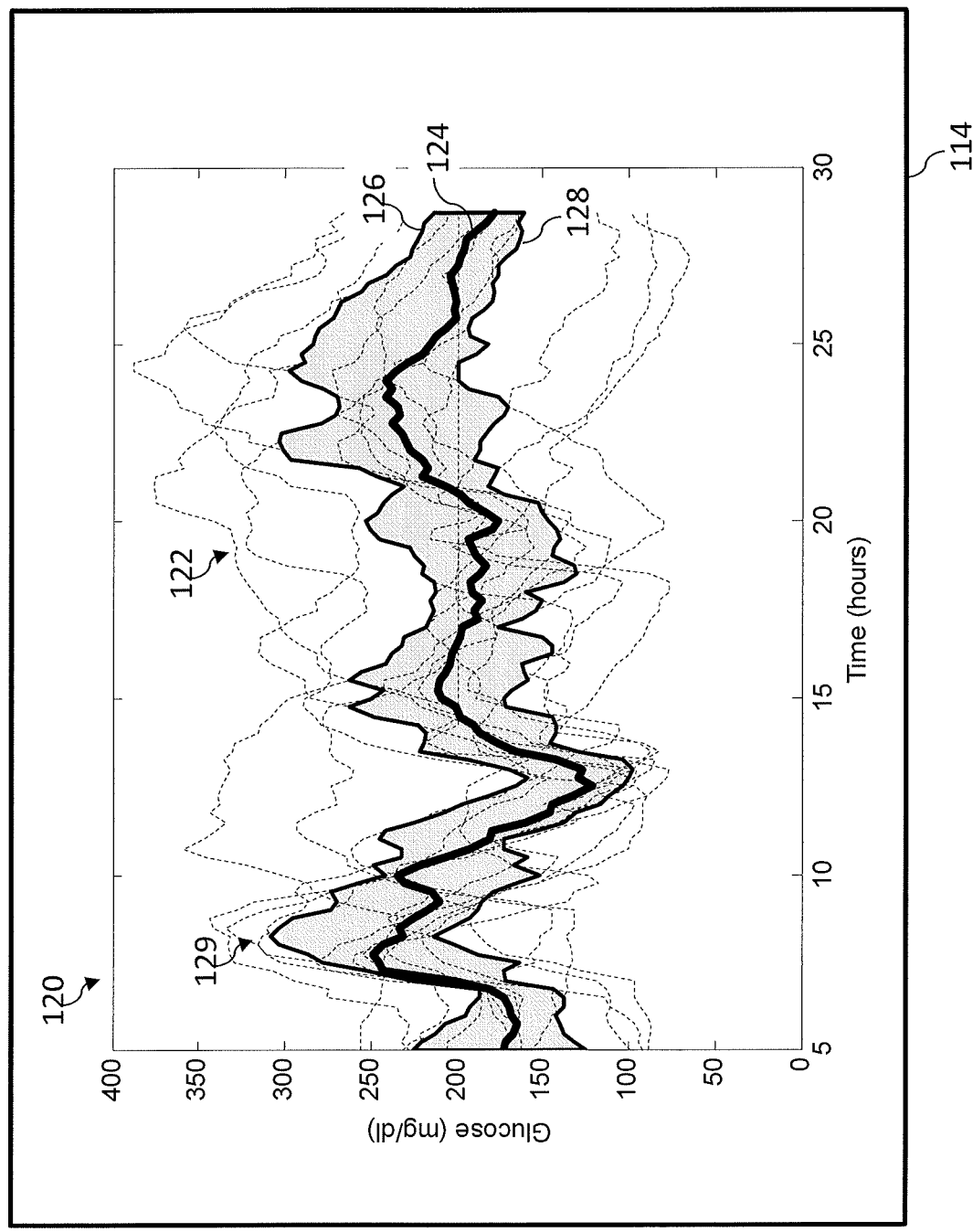
FIG. 2 schematically depicts a display provided with a human machine interface according to one or more embodiments shown and described herein.

Referring collectively to FIGS. 1 and 2, in one embodiment, the one or more processors 110 can execute machine readable instructions to display an Ambulatory Glucose Profile (AGP), or Modal Day on the human machine interface 114. A Modal Day plot 120, as depicted in FIG. 2, can display multiple periods of time indexed glucose data normalized to a specific time of day (e.g., 5:00) and plotted with increasing time along the horizontal axis. Accordingly, the Modal Day plot 120 can simultaneously display multiple days of glucose data (24 hour period) with each day of glucose data in the Modal Day plot 120 corresponding to a Modal Day data curve 122 (generally indicated in FIG. 2 as a dashed line). The Modal Day data curves 122 can be statistically evaluated to identify any patterns that may exist in the glucose data. For example, the median 124 can be calculated and overlaid upon the Modal Day data curves 122 in the Modal day plot 120. Similarly, the third quartile 126 and the first quartile 128 can be calculated and overlaid upon the data curves 122. In further embodiments, the Modal day plot 120 can include additional statistics such as, for example, the mean and standard deviation for the time period. Alternatively or additionally, the Modal Day plot 120 may include the range of the glucose data, maximum of the glucose data, minimum of the glucose data, or raw data for each time period.

The Modal Day plot 120 can be utilized to automatically display a dominant glucose pattern 129. For example, the dominant glucose pattern 129 can be seen from 7:00 to about 13:00 and may represent a meal rise due to breakfast, for example. Accordingly, a PwD may be able to adjust behavior by identifying the dominant glucose pattern 129 that is displayed in the Modal Day plot 120. However, the remaining portions of data curves 122 fail to conform to any distinct pattern. Accordingly, the Modal Day plot 120 does not display any pattern in the portion of the time period falling outside of the dominant glucose pattern 129. Additionally, it is noted that the Modal Day plot 120 can obscure the display of the data curves 122 by overlaying data. Moreover, in some embodiments, only reporting statistics are displayed.

Figure 3:
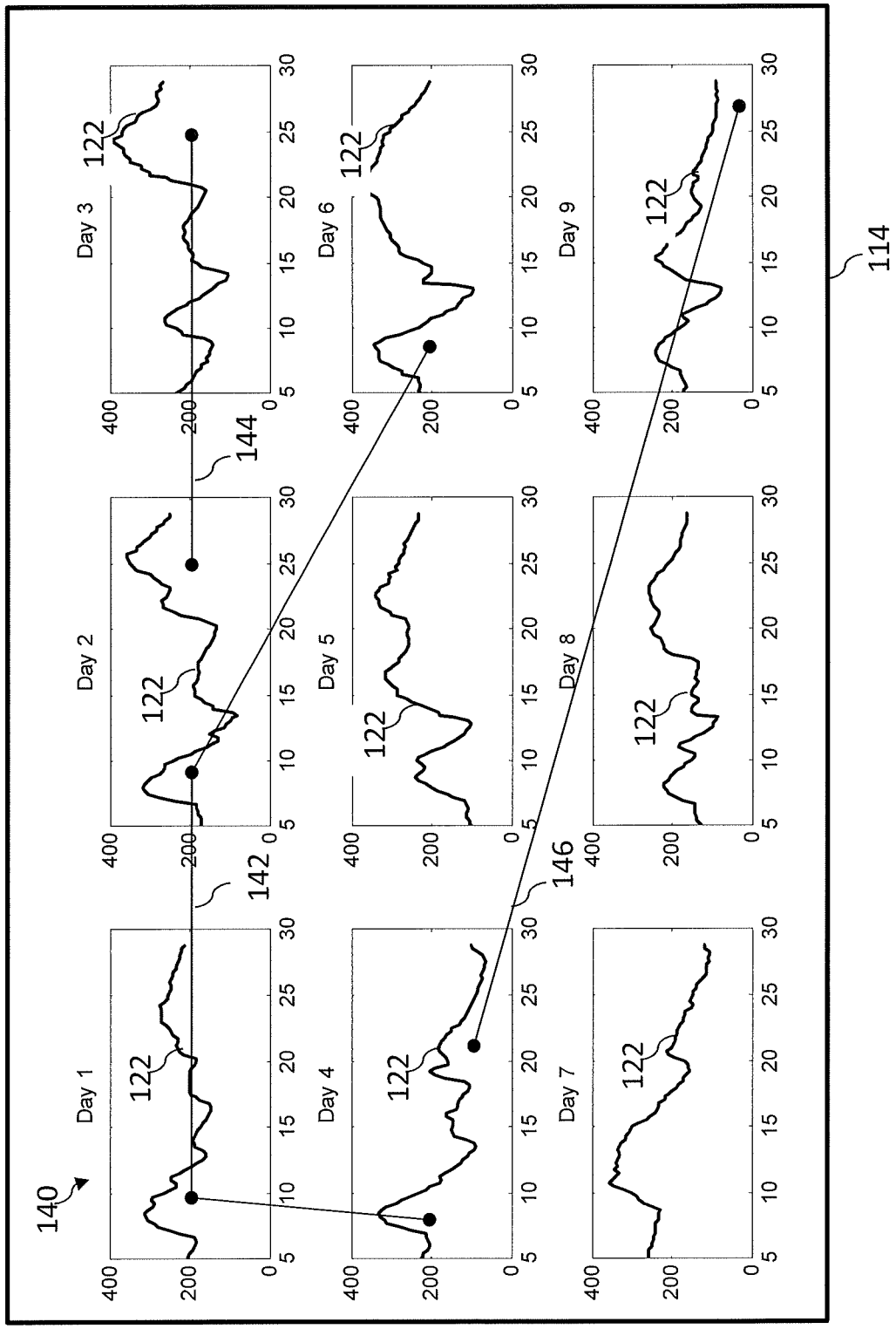
FIG. 3 schematically depicts a display provided with a human machine interface according to one or more embodiments shown and described herein.

Referring collectively to FIGS. 1 and 3, in one embodiment, the one or more processors 110 can execute machine readable instructions to display a timeline grid 140 on the human machine interface 114. Specifically, the timeline grid 140 can simultaneously display multiple data curves 122 each displayed in a separate section (e.g., Day 1, Day 2, Day 3, Day 4, Day 5, Day 6, Day 7, Day 8, and Day 9). Patterns are displayed and can be linked together. For example, the displayed timeline grid 140 can be visually scanned. Each day that exhibits similar patterns can be linked, i.e., the corresponding portions of the data curves 122 can be selected and linked together in the memory 112. For example, Day 1, Day 2, Day 4, and Day 6 exhibit similar glucose values between about 5:00 and 12:00 and can be linked by a first link 142. Day 2, and Day 3 exhibit similar glucose values between about 22:00 and 27:00 and can be linked by a second link 144. Day 4, and Day 9 exhibit similar glucose values between about 20:00 and 24:00 and can be linked by a third link 146. Linking the data curves 122 is generally a manual process that can be relatively inefficient and can add difficulty for the user. Moreover, the timeline grid 140 can be utilized to display glucose data for a single sensor lifetime such as, for example, less than or equal to about nine days, or from about three days to about seven days. As the number of time periods displayed in the timeline grid 140 increases, the effectiveness of the timeline grid 140 for displaying patterns can decrease and patterns may be missed.

Figure 4:
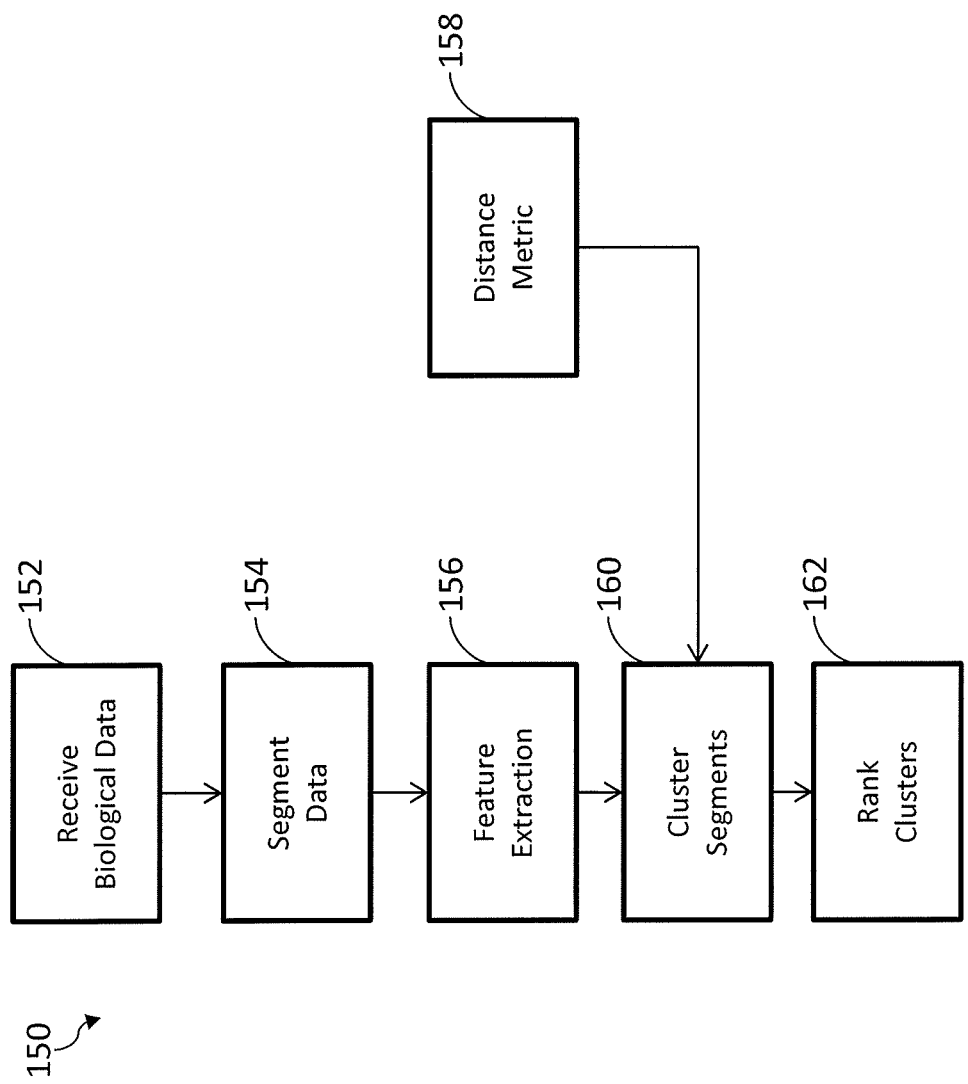
FIG. 4 schematically depicts a pattern enhancement algorithm according to one or more embodiments shown and described herein.

Referring collectively to FIGS. 1 and 4, in another embodiment, the one or more processors 110 can execute machine readable instructions to execute a pattern enhancement algorithm 150 to automatically enhance patterns that may exist within biological data such as blood glucose data or CGM data. As is described in greater detail herein, once the patterns in the biological data are enhanced, the patterns in the biological data can automatically be displayed data on the human machine interface 114.

Figure 5:
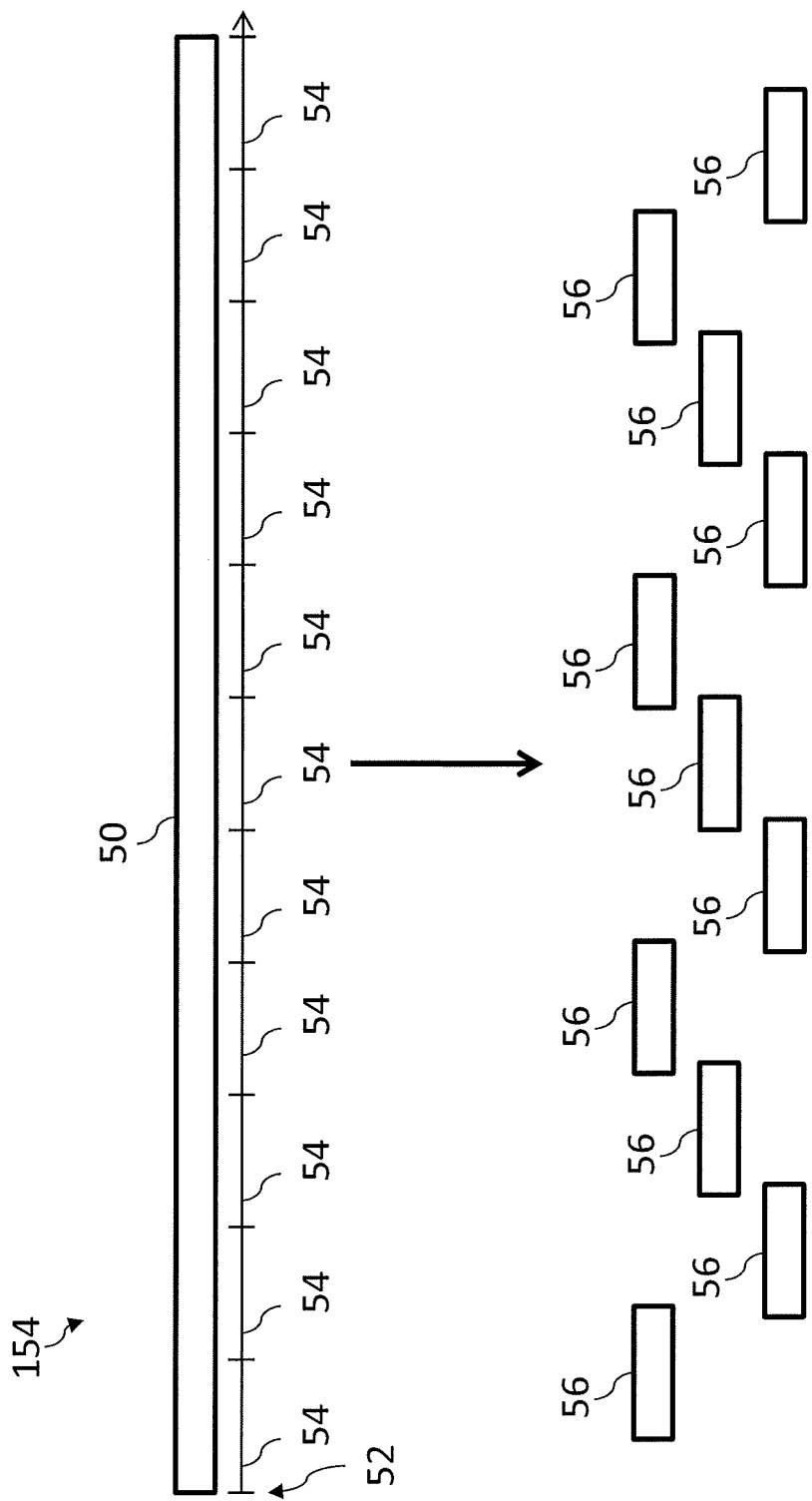
FIG. 5 schematically depicts biological data and segments of interest according to one or more embodiments shown and described herein.

Referring collectively to FIGS. 4 and 5, the pattern enhancement algorithm 150 generally enhances data patterns by clustering similar biological outcomes, i.e., glucose values, to identify the inputs that may have caused the biological response. The pattern enhancement algorithm 150 comprises a process 152 for receiving biological data indicative of ambulatory biological information sampled over time from one or more subjects. The biological data 50 can include a time index 52 that is suitable to associate the biological data 50 with the time and/or date that the ambulatory biological information was sampled such as, for example, day, month, hour, minute, second, and the like. For example, each instance of the biological data 50 can be associated with a time and a date indicative of the time and date that the ambulatory biological information was sampled.

In addition to biological data 50, the pattern enhancement algorithm 150 can be utilized to enhance patterns that exist in any combination of continuous data, semi-continuous data and/or discrete data. Sources of semi-continuous data may include, for example, medication delivery device infusion profiles, bolus profiles, energy expenditure measurements, heart-rate movement, or any other data related to behaviors that may influence the health of a PwD. Sources of discrete data may include, for example, data tags, day of the week, month, season, sensor production lot number, insulin lot number, pump reusable lot numbers, or any other data or metadata related to behaviors that may influence the health of a PwD. Accordingly, the pattern enhancement algorithm 150 can also receive any other type continuous data, semi-continuous data and/or discrete data at process 152.

The pattern enhancement algorithm 150 comprises a process 154 for segmenting data. Specifically, with reference to FIG. 5, at process 154 the biological data 50 can be divided into segments of interest 56 according to the time index 52. The segments of interest 56 can each be a time window of data that corresponds to a predetermined duration, a predetermined start time, a predetermined end time or combinations thereof. For example, the biological data 50 can be divided into segments of interest 56 that each correspond to a twenty-four hour day with a common start and end time. Alternatively, the biological data 50 can be divided into segments of interest 56 that each corresponds to a four hour time period or six hour time period of data to, for example, segment postprandial glucose profiles. In another embodiment, the biological data 50 can be divided into segments of interest 56 that each corresponds to eight hour time period or ten hour time period of data to, for example, segment nocturnal glucose profiles.

It is noted that the biological data 50 can be divided into segments of interest 56 having any length of time sufficient to capture a biologically meaningful event. Specifically, the segments of interest 56 can be tailored to a length of time that corresponds to any known biological process such as, for example, glucose response to a correction bolus, periods of exercise, glucose response after exercise, postprandial, before, during and/or after a therapy change and the like. Accordingly, although the embodiments described herein may utilize twenty-four hour time periods, other segments of time may be used without deviating from the scope of the disclosure. Moreover, it is noted that each of the segments of interest 56 can be separate (no duplicated data) or overlap. The segments of interest 56 may be selected based upon a uniform start time (e.g., 5 AM each day) or may be selected based on a contextual tag, or event, such as, for example, a meal tag or bolus event. When the biological data 50 is provided through CGM, the segments of interest 56 may contain raw continuous glucose measurements or the filtered signal along with additional relevant contextual data.

Referring collectively to FIGS. 4 and 5, the pattern enhancement algorithm 150 comprises a process 156 for extracting a set of features from each of the segments of interest 56. Specifically, each of the segments of interest 56 can be transformed automatically into a set of features that is a reduced representation of the segments of interest 56 according to a mathematical algorithm. The mathematical algorithm can be any algorithm that extracts relevant information from the segments of interest 56 in order to perform the pattern recognition. The mathematical algorithm can be, for example, a Principal Component Analysis (PCA), a Kernel PCA, a wavelet analysis, a frequency analysis, or any other algorithm suitable to extract meaningful features. The set of features can be extracted from any combination of continuous data, semi-continuous data and/or discrete data. Moreover, a set of features extracted from biological data 50 can be supplemented with discrete data, i.e., discrete data can be appended directly to calculated vectors. The set of features can be utilized by a distance metric to identify and enhance patterns in the biological data 50.

Accordingly, the pattern enhancement algorithm 150 further comprises a process 158 for determining a distance metric. Specifically, the distance metric can be any function capable of indicating the degree of similarity between each of the segments of interest 56. In some embodiments, the function for determining the distance metric between each of the segments of interest 56 can be applied to the set of features of the segments of interest 56. For example, the distance metric can be calculated as the sum of squared distance between the set of features of the segments of interest 56. Further, functions for determining distance metrics include, but are not limited to, the sum of absolute distance, Mahalanobis distance, Manhattan distance, maximum norm, or any other common metrics known for evaluating sets of features. In further embodiments, the distance metric may be determined based upon processed or filtered biological data (e.g., calibrated and filtered glucose data). The distance metric may also be calculated based upon the raw biological data.

The distance metric may be calculated from the biological data 50 alone. Alternatively or additionally, the distance metric may be based on the distance between contextual data and/or contextual data tags. For example, the distance metric may be calculated from CGM data and carbohydrate intake located near a specific insulin tag. The distance metric may be based upon the entire segment of interest, or a subset of the segment of interest. Accordingly, the distance metric and the set of features can be used by the pattern enhancement algorithm 150 to group individual segments of interest 56.

The pattern enhancement algorithm 150 comprises a process 160 for clustering the segments of interest 56. Specifically, a clustering algorithm can be applied automatically to cluster the segments of interest 56 into groups of clustered segments. Once clustered, similar segments of interest 56 are grouped in each the clustered segments. Accordingly, the groups of clustered segments enhance and identify patterns that exist within the data. In some embodiments, the clustering algorithm can determine both the number of clusters and the segments of interest 56 that are assigned to each cluster based upon the distance metric. The clustering algorithm used may include functions for determining the number of clusters such as, for example, a Schwarz Criterion, a Bayesian Information Criterion, an Akaike Information Criterion, or any other optimizer. The clustering algorithm used may include functions for assigning segments of interest 56 to cluster such as, for example, K-means, Hierarchical clustering (using either an agglomerative or divisive method or some combination of both), Gaussian mixture modeling, Normalized Cuts, or other any clustering algorithm. It is noted, that the example described below utilizes for K-means clustering, but other clustering algorithms may be utilized without deviating from the scope of the present disclosure.

According to the embodiments described herein, the pattern enhancement algorithm 150 may comprise a process 162 for ranking the groups of clustered segments. In one embodiment, the groups of clustered segments can be associated with an importance ranking based on the number of segments in the group. The importance ranking can also be based upon the occurrence of an event such as, for example, hypoglycemia or hyperglycemia. For example, a group of clustered segments can be associated with a relatively high importance ranking, compared to other groups of clustered segments, when the group includes a larger number of clustered segments, which can be indicative of a common behavior, than the other groups and is coincident with one or more instances of hypoglycemic events or hyperglycemic events. A group of clustered segments associated with a relatively high importance ranking can be indicative of behavior that needs to be addressed by the HCP or PwD. Accordingly, the groups of clustered segments clusters can be ranked based on the need for the HCP to adjust therapy or provide education to address the problem.

The group of clustered segments can also be associated with dates to identify patterns that can occur on regular basis such as, for example, weekly, weekday vs. weekend, workday vs. non-workday, monthly or seasonally. Furthermore, the clustered segments can be aggregated based upon discrete data, for example, sensor production lot numbers, insulin lot numbers, or pump reusable lot numbers in order to help identify potential manufacturing defects.

As is noted above, once the patterns in the data are enhanced by generating clustered segments, the patterns in the biological data can automatically be displayed on the human machine interface 114 by the one or more processors 110. The displayed clustered segments enhance the patterns that exist in the data and that may have been obscured. Accordingly, a user such as a HCP or a PwD can more readily identify patterns in the biological data.

Figure 6:
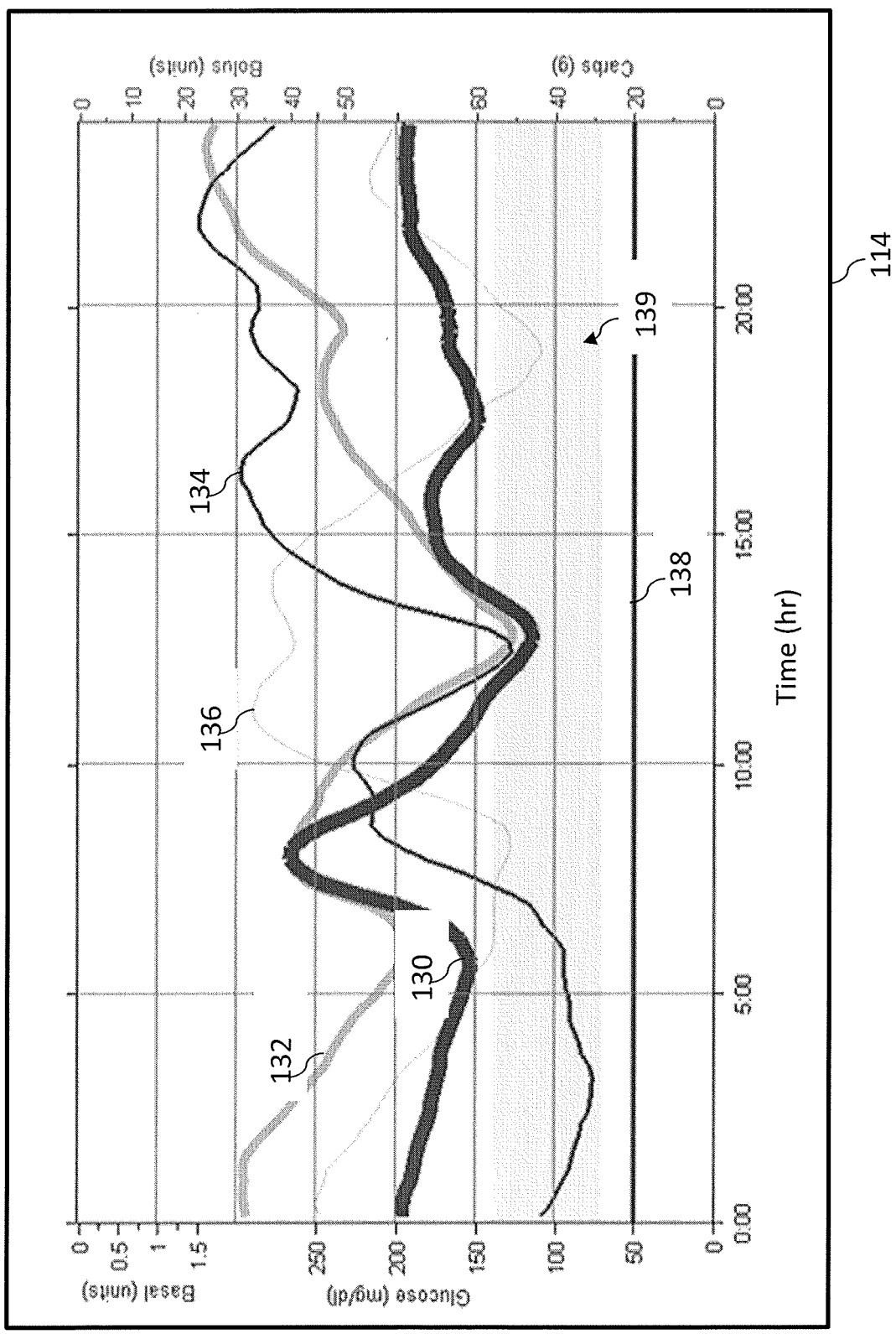
FIG. 6 schematically depicts a display provided with a human machine interface according to one or more embodiments shown and described herein.
Figure 7:
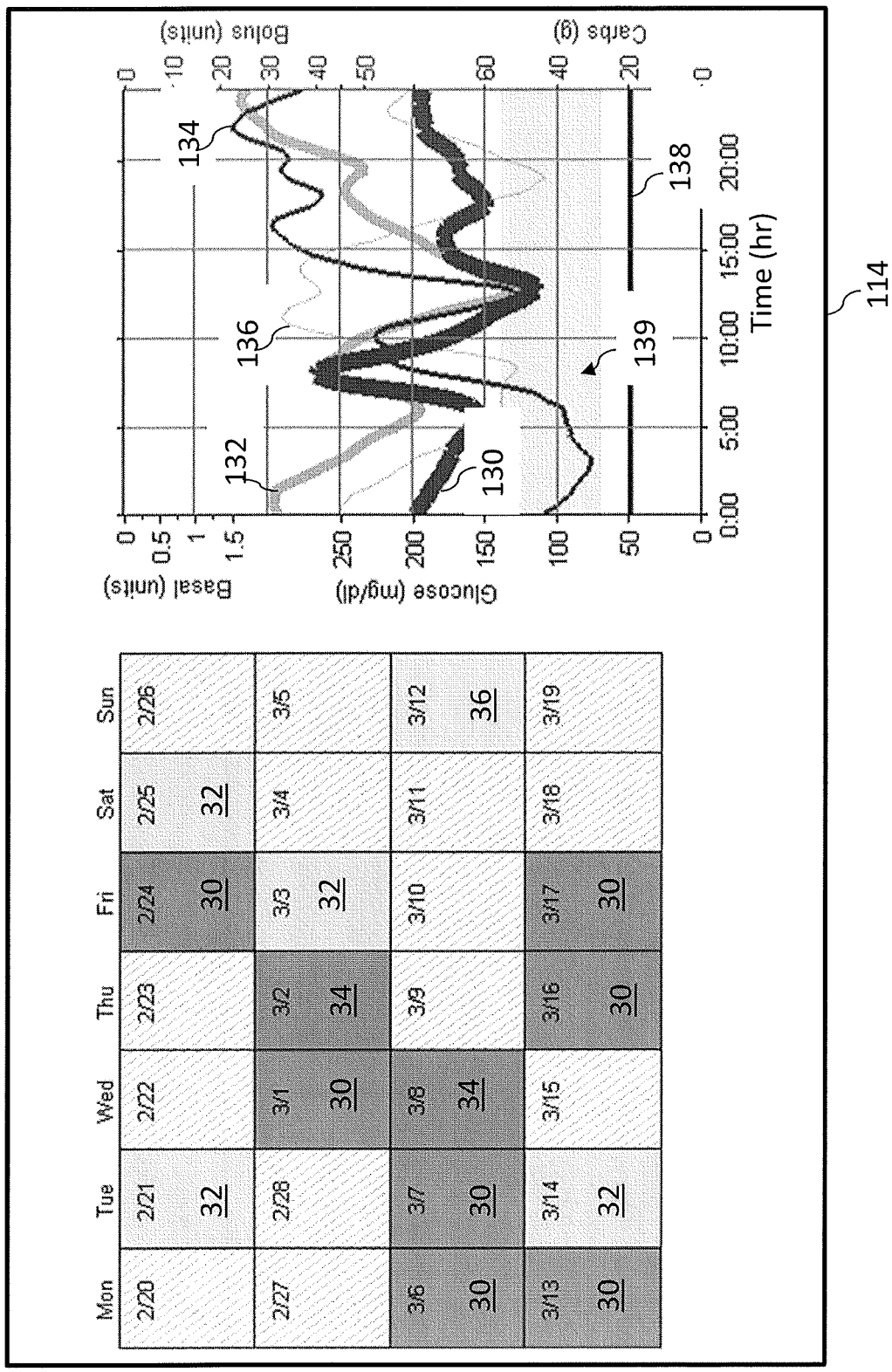
FIG. 7 schematically depicts a display provided with a human machine interface according to one or more embodiments shown and described herein.

Referring collectively to FIGS. 6 and 7, the mean of each group of clustered segments can be displayed automatically on the human machine interface 114. Specifically, a first cluster center 130 corresponds to the mean of a first group of clustered segments, a second cluster center 132 corresponds to the mean of a second group of clustered segments, a third cluster center 134 corresponds to the mean of a third group of clustered segments, and a third cluster center 136 corresponds to the mean of a fourth group of clustered segments. Accordingly, the biological data may be summarized by only displaying the cluster centers 130, 132, 134, 136, which enhance the patterns that exist within the biological data. Moreover, the displayed line width of each of the cluster centers 130, 132, 134, 136 can be indicative of each of their importance ranking For example, the width of the cluster centers 130, 132, 134, 136 can be proportional to the number of segments included in the cluster. Specifically, the width of the first cluster center 130, depicted in FIG. 6, indicates that the first group of clustered segments includes the highest number of clustered segments. Moreover, as depicted in FIG. 6, the width of the second cluster center 132 indicates that the second group of clustered segments includes the second highest number of clustered segments, the width of the third cluster center 134 indicates that the third group of clustered segments includes the third highest number of clustered segments, and the width of the fourth cluster center 136 indicates that the fourth group of clustered segments includes the lowest number of clustered segments. Accordingly, the displayed line width of each of the cluster centers 130, 132, 134, 136 can enhance consistent behaviors with relatively thick lines and outlier behaviors with relatively thin lines. In further embodiments, cluster centers 130, 132, 134, 136 can be color coded according to importance rankings.

Summary statistics may also be calculated for each group of clustered segments and automatically displayed on the human machine interface 114 by the one or more processors 110. The summary statistics may include the mean, median, standard deviation, mean absolute difference, range, quartiles or any other suitable statistics. The statistics may also include percentage of time in hyperglycemia, percentage of time within a target range, percentage of time below a threshold, or percentage of time above a specific threshold, for example. Summary statistics may also include parameters based on the number of groups that represent the biological data, the number of data segments in each group, or any other parameters related to the distribution of data segments within the groups of clustered segments. The summary statistics may be used as metrics to characterize the state of the PwD as well as indicators for potential therapy adjustments.

Additionally, regions of importance such as, for example, hyperglycemia, hypoglycemia, glucose target ranges, and the like can be displayed automatically on the human machine interface 114. For example, a hypoglycemia threshold 138 and a target glucose concentration range 139 can be displayed on the human machine interface 114. The human machine interface 114 can also display contextual data associated with the clustered data segments such as, for example, meal tags, carbohydrate intake, insulin injections, or other relevant contextual data. It is noted that, while FIGS. 6 and 7 only depict the cluster centers, the cluster centers can be overlaid upon curves indicative of the clustered segments and/or the segments of interest.

Referring to FIG. 7, a calendar 20 can also be displayed by the human machine interface 114 to identify weekly or monthly patterns. In one embodiment, the calendar 20 can be coded to indicate the dates that correspond to cluster centers 130, 132, 134, 136. Each code can be a color, a gradient, a shape, an alphanumeric, or any other visual indicator sufficient to distinguish the cluster code from other objects displayed by the human machine interface 114. Specifically, dates coded with a first cluster code 30 include one or more clustered segments that correspond to the first cluster segment 130, dates coded with a second cluster code 32 include one or more clustered segments that correspond to the second cluster center 132, dates coded with a third cluster code 34 include one or more clustered segments that correspond to the first cluster segment 134, and dates coded with a fourth cluster code 36 include one or more clustered segments that correspond to the fourth cluster center 136. Accordingly, the calendar 20 can be provided with cluster codes to display the similarity between the clustered segments for the dates on the calendar 20. In some embodiments, entries from calendar software such as Microsoft Outlook® or Google Calendar® can be imported and displayed with the calendar 20 to help identify behavior patterns that may be causes for the glucose patterns. Alternatively, the data from the clustered segments may be exported to a format so that it can be imported into calendar software. In further embodiments, the calendar 20 can indicate visually missed events such as, for example, insulin boluses, activities or meals.

Referring collectively to FIGS. 1 and 7, the one or more processors 110 can accept input indicative of a selection made by a user. In one embodiment, the one or more processors 110 can receive a selection signal indicative of the selection of a date on the calendar 20. The one or more processors 110 can respond to the selection signal by displaying the segments of interest that were sampled on the corresponding date. In another embodiment, the one or more processors 110 can receive a cluster signal indicative of the selection of cluster center or code on the calendar 20 corresponding to a cluster center. The one or more processors 110 can respond to the cluster signal by displaying the clustered segments that are associated with the cluster center.

In order that the embodiments described herein may be more readily understood, reference is made to the following example which is intended to illustrate the embodiments described herein, but not limit the scope thereof.

Figure 8:
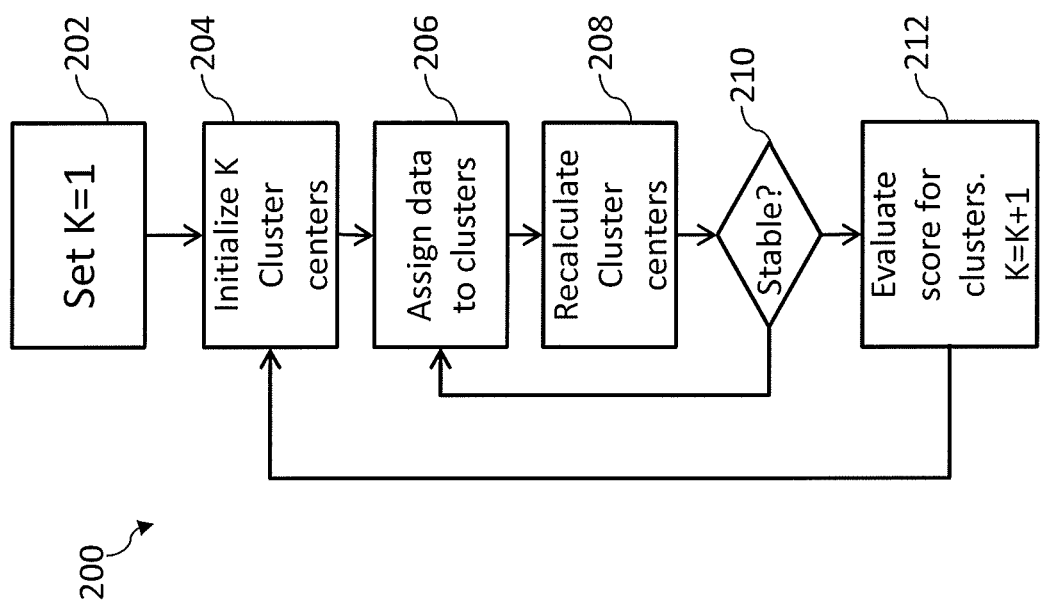
FIG. 8 schematically depicts a pattern enhancement algorithm according to one or more embodiments shown and described herein.

Referring now to FIG. 8, an exemplary pattern enhancement algorithm 200 was executed by a processor to automatically group a CGM data indicative of ambulatory glucose levels sampled over time into groups of clustered segments. Filtered CGM data were received by the processor and segmented into segments of interest. Each segment of interest was selected to begin at 5:00 AM, so that the overnight data would remain continuous, and was of substantially equal length (about 24 hours). A set of features was extracted from each of the segments of interest. As a result, each of the segments of interest were compressed from vectors having a length of about 1440 (number of minutes in a day) into vectors having a length of about 20 by using the first 20 Eigenvectors.

The exemplary pattern enhancement algorithm 200 included an iterative K-means algorithm for clustering and utilized a Schwarz Criterion to determine the number of groups of clustered segments. At process 202, the exemplary pattern enhancement algorithm 200 was initialized to perform a first iteration with the number of clusters k equal to 1. At process 204, the cluster centers were calculated for the number of clusters k. Following the calculation of the cluster centers, the segments of interest were assigned to the groups at process 206. After the groups were assigned, the cluster centers were recalculated using the groups of segmented clusters at process 208. At process 210, a stability check was performed. When the solutions for K-means algorithm failed to converge, process 206 was repeated. When the solutions for K-means algorithm did not change for multiple iterations, process 212 was performed to determine the Schwartz Criterion. After process 212, process 204 was repeated for a predetermined number of iterations and the groups of clustered segments corresponding to the minimum Schwartz criterion was selected as the final result.

Figure 9:
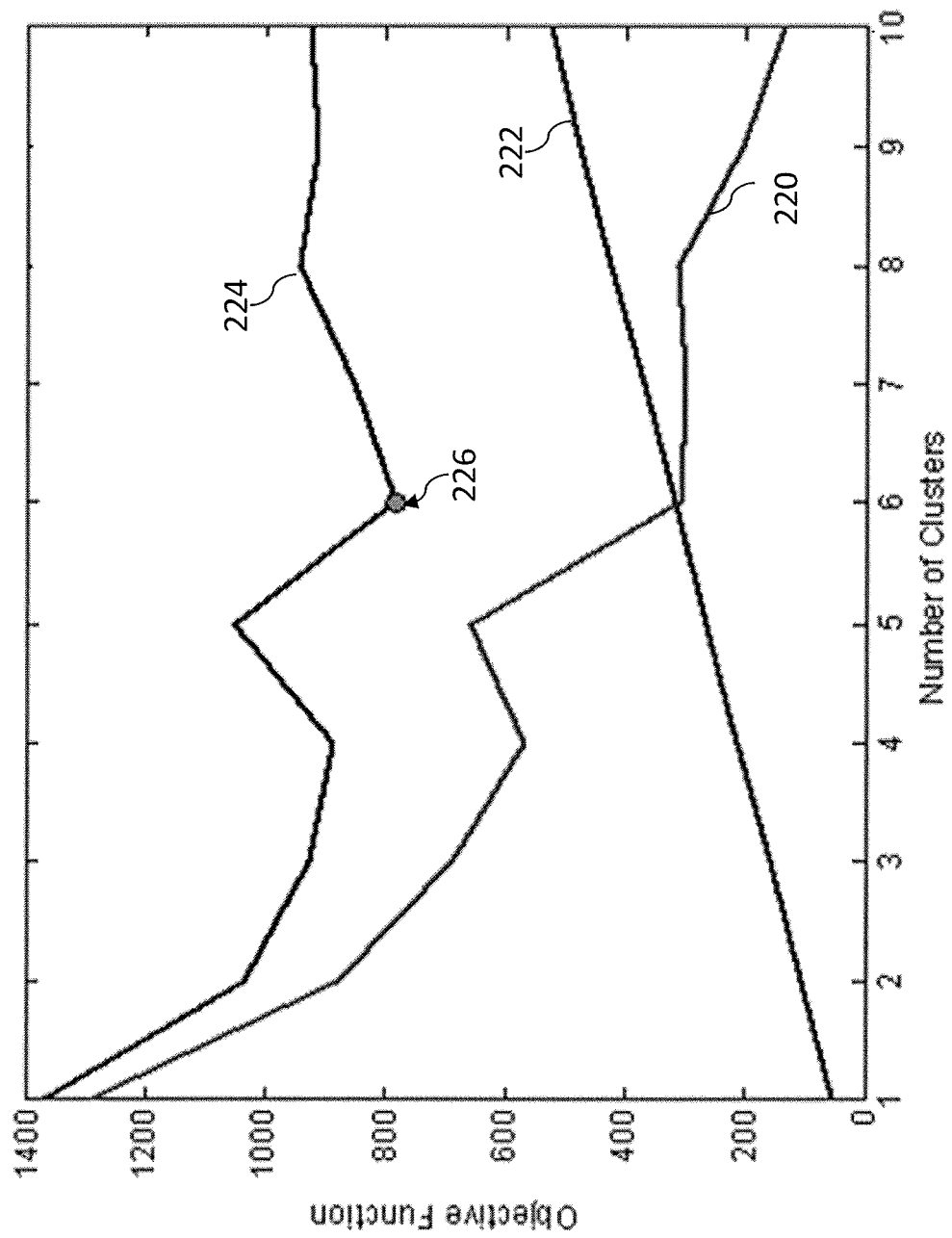
FIG. 9 graphically depicts the output from an optimizer according to one or more embodiments shown and described herein.

Referring now to FIG. 9, the output from the Schwarz Criterion 224 is graphically depicted. The number of clusters was evaluated by using the Schwarz Criterion 224, which added a penalty term 222 to the optimization equation that was be based on the number of groups of clustered segments.

Given:

X=the set of observations;

n=number of data points in X, the number of observations;

k=number of clusters;

m=the number of dimensions;

$dist(X_k, \overline{X_k})$=the distance function calculated between all the segments in cluster k and the mean of cluster; and $\lambda$=a tuning parameter to adjust the balance between the distance based metric and the penalty term.

The Schwarz Criterion 224 was calculated with the following equation.

$$SIC = \sum_k dist(X_k, \overline{X_k}) + \lambda mk\ln(n)$$

The number of groups of clustered segments were determined by combining the quality metric 220 which measures how well the clustered segments fit the segments of interest with a penalty term 222 that penalizes based, in part, on the number of groups of clustered segments. "Quality" refers to the value of $$\sum_k dist(X_k, \overline{X_k})$$

and "Penalty" refers to the value of $\lambda mk \ln(n)$. The minimum value 226 for the Schwarz Criterion 224 occurred when six groups of clustered segments were used.

It should now be understood that, the embodiments described herein can be utilized to cluster data and automatically display cluster centers such that patterns that exist within the larger set of data are enhanced. The displayed cluster centers can allow patterns, sub-patterns, or behaviors to easily be identified. Accordingly, the displayed cluster centers can enhance and identify information that may otherwise be averaged out or obscured, e.g., when combining the multiple days of data into the AGP or modal day.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue. While various embodiments of systems and methods for automatically displaying patterns in glucose data have been described in considerable detail herein, the embodiments are merely offered by way of non-limiting examples of the disclosure described herein. It will therefore be understood that various changes and modifications may be made, and equivalents may be substituted for elements thereof, without departing from the scope of the disclosure. Indeed, this disclosure is not intended to be exhaustive or to limit the scope of the disclosure.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. Other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

The invention claimed is:

1. A collection system for automatically displaying patterns in glucose data of one or more patients, the collection system comprising:
one or more processors;
an electronic display communicatively coupled to the one or more processors; and
machine readable instructions that are executed by the one or more processors, wherein the machine readable instructions cause the one or more processors to:

receive a glucose data signal indicative of ambulatory glucose levels sampled over multiple days and determined from a body fluid of the one or more patients via a glucose meter communicatively coupled to the one or more processors;

divide the glucose data signal into segments of interest;

transform, automatically, each of the segments of interest into a set of features according to a mathematical algorithm;

append discrete data to the set of features;

cluster, automatically, the segments of interest into groups of clustered segments according to a clustering algorithm, wherein each group of clustered segments is associated with an importance ranking based on a number of segments in a respective group, wherein the segments of interest are grouped in the groups of clustered segments based at least in part upon the set of features and a cluster center is associated with one of the groups of clustered segments, wherein each cluster center corresponds to a mean of one of the groups of clustered segments and includes a width indicative of the importance ranking and corresponding number of segments in the respective group, and wherein each cluster center width is proportional to the corresponding number of segments in the respective group; and present, automatically, the cluster center and corresponding width of each one of the groups of clustered segments on the electronic display based on the importance ranking corresponding to the number of segments in the respective group of each cluster center, wherein displayed cluster centers identify information regarding patterns, sub-patterns or behaviors in the glucose data of the one or more patients that otherwise is averaged out or obscured when the ambulatory glucose levels sampled over multiple days are combined into an ambulatory glucose profile or a modal day plot.

2. The collection system of claim 1, wherein the one or more processors are communicatively coupled to a medication delivery device.

3. The collection system of claim 1, wherein the one or more processors are communicatively coupled to a mobile phone, a mobile computing device, a portable digital assistant, a desktop computer, a server, or combinations thereof.

4. The collection system of claim 1, wherein the glucose data signal is associated with a time index indicative of a point in time, a date, or both that the glucose data signal was sampled and the glucose data signal is divided into the segments of interest according to the time index.

5. The collection system of claim 4, wherein each of the segments of interest correspond to a twenty-four hour day with a common start time and end time.

6. The collection system of claim 4, wherein each of the segments of interest correspond to a glucose profile corresponding to a biologically meaningful event.

7. The collection system according to claim 1, wherein the machine readable instructions cause the one or more processors to:

transform, automatically, a medication delivery device infusion profile, a bolus profile, an energy expenditure measurement, a heart-rate movement, a meal tag, or combination thereof into a supplemental set of features; and append the supplemental set of features to the set of features.

8. The collection system according to claim 1, wherein machine readable instructions cause the one or more processors to:

transform a sensor production lot number, an insulin lot number, a pump reusable lot number, or combination thereof into a supplemental set of features; and append the supplemental set of features to the set of features.

9. The collection system according to claim 1, wherein the mathematical algorithm comprises a Principal Component Analysis (PCA), a Kernel PCA, a wavelet analysis, a frequency analysis, or a combination thereof.

10. The collection system according to claim 1, wherein the clustering algorithm comprises an optimizer.

11. The collection system according to claim 1, wherein the clustering algorithm comprises a K-means algorithm, a Hierarchical clustering algorithm, a Gaussian mixture modeling algorithm, a Normalized Cuts algorithm, or a combination thereof.

12. The collection system according to claim 1, wherein the machine readable instructions cause the one or more processors to:

rank, automatically, the groups of clustered segments based upon the occurrence of an event.

13. The collection system according to claim 1, wherein the machine readable instructions cause the one or more processors to:

rank, automatically, the groups of clustered segments according to a quantity of segments of interest associated with the groups of clustered segments.

14. The collection system of claim 12, wherein the cluster center is color coded according to a ranking of the groups of clustered segments.

15. The collection system according to claim 1, wherein the cluster center is displayed with a line width that is correlated to a quantity of segments of interest associated with the cluster center.

16. The collection system according to claim 1, wherein the cluster center is overlaid upon curves indicative of the segments of interest.

17. The collection system according to claim 1, wherein the machine readable instructions cause the one or more processors to present, automatically, a calendar on the electronic display, wherein the calendar is coded to indicate a date that corresponds to the cluster center.

18. The collection system of claim 17, wherein the machine readable instructions cause the one or more processors to:

receive, automatically, a selection signal indicative of a selection of a selected date on the calendar; and present, automatically, the segments of interest that were sampled on the selected date.

19. The collection system according to claim 1, wherein the machine readable instructions cause the one or more processors to:

receive, automatically, a selection signal indicative of a selection of a selected cluster center; and present, automatically, the segments of interest that correspond to the selected cluster center on the electronic display.

20. A method for automatically displaying patterns in biological monitoring data of one or more subjects, the method comprising:

having, via machine readable instructions being executed by one or more processors, the one or more processors performing the processes of:

receiving biological data indicative of ambulatory biological information sampled over multiple days and determined from a body fluid of the one or more subjects via a glucose meter communicatively coupled to the one or more processors, wherein the biological data is aggregated from multiple test subjects and comprises a time index;

dividing the biological data into segments of interest according to the time index;

transforming, automatically, each of the segments of interest into a set of features according to a mathematical algorithm; and clustering, automatically, the segments of interest into groups of clustered segments according to a clustering algorithm, wherein each group of clustered segments is associated with an importance ranking based on a number of segments in a respective group, wherein the clustering algorithm calculates a distance metric based at least in part upon the set of features of each of the segments of interest such that similar segments of interest are grouped in one of the groups of clustered segments and calculates a cluster center that is associated with one of the groups of clustered segments, wherein each cluster center corresponds to a mean of one of the groups of clustered segments and includes a width indicative of the importance ranking and corresponding number of segments in the respective group, and wherein each cluster center width is proportional to the corresponding number of segments in the respective group; and presenting, automatically on an electronic display communicatively coupled to the one or more processors, the cluster center and corresponding width of each one of the groups of clustered segments based on the importance ranking corresponding to the number of segments in the respective group of each cluster center, wherein displayed cluster centers identify information regarding patterns, sub-patterns or behaviors in the glucose data of the one or more subjects that otherwise is averaged out or obscured when the ambulatory biological information sampled over multiple days are combined into an ambulatory glucose profile or a modal day plot.

21. The method of claim 20, wherein the distance metric is based upon a sum of squared distance, a sum of absolute distance, a Mahalanobis distance, a Manhattan distance, a maximum norm, or a combination thereof.

* * * * *